United States Patent
Goldman (10) Patent No.: US 9,936,899 B2
(45) Date of Patent: Apr. 10, 2018

(54) TREMOR REDUCTION SYSTEM AND DEVICE

(71) Applicant: David A. Goldman, Yorktown Heights, NY (US)

(72) Inventor: David A. Goldman, Yorktown Heights, NY (US)

(73) Assignee: Joseph Goldman, New York, NY (US)

( * ) Notice: Subject to any disclaimer, the term of this patent is extended or adjusted under 35 U.S.C. 154(b) by 794 days.

(21) Appl. No.: 14/502,090

(22) Filed: Sep. 30, 2014

(65) Prior Publication Data

US 2015/0100004 A1 Apr. 9, 2015

Related U.S. Application Data

(60) Provisional application No. 61/887,675, filed on Oct. 7, 2013.

(51) Int. Cl.
*A61H 23/00* (2006.01)
*A61B 5/11* (2006.01)
*A61F 5/30* (2006.01)
*A61B 34/00* (2016.01)

(52) U.S. Cl.
CPC ............ *A61B 5/1101* (2013.01); *A61B 34/75* (2016.02); *A61H 23/006* (2013.01); *A61F 5/30* (2013.01); *A61H 2205/06* (2013.01)

(58) Field of Classification Search
CPC .. A61H 23/004; A61H 39/04; A61H 23/0254; A61H 23/0263; A61H 23/006; A61F 5/30; A61B 5/1101; A61B 34/75

USPC .......................................................... 606/204
See application file for complete search history.

(56) References Cited

U.S. PATENT DOCUMENTS

| | | | | |
|---|---|---|---|---|
| 3,050,064 | A * | 8/1962 | Moore | A61B 17/1325 606/203 |
| 6,251,089 | B1 * | 6/2001 | Kuznets | A61H 7/005 601/112 |
| 6,361,549 | B1 * | 3/2002 | Asatourian | A61F 5/30 606/204 |
| 8,353,927 | B2 * | 1/2013 | Lampropoulos | A61B 17/1325 24/486 |
| 9,452,287 | B2 * | 9/2016 | Rosenbluth | A61N 1/0492 |
| 2003/0006357 | A1 * | 1/2003 | Kaiser | F16F 7/1005 248/550 |
| 2004/0098037 | A1 * | 5/2004 | Grey | A61H 39/04 606/204 |

(Continued)

*Primary Examiner* — Justine Yu
*Assistant Examiner* — Douglas Sul
(74) *Attorney, Agent, or Firm* — Ware, Fressola, Maguire & Barber LLP (57) ABSTRACT

A tremor reduction device has a mechanical flap having a flap portion arranged to apply pressure on part of an inner arm in order to reduce tremor. The pressure can be manually adjusted by moving a rod in a channel in the tremor reduction device. The tremor reduction device has a case for pivotably mounting the mechanical flap and the pressure is at least partly determined by the angle of the mechanical flap relative to the case. The rod has a tapered section and the mechanical flap has a pin in contact the tapered section for changing the angle of the mechanical flap. Optionally a sensor is placed near the pressure applying location to sense the tremor and to provide a sensing signal to a driving mechanism which causes the rod to move in order to adjust the pressure.

14 Claims, 5 Drawing Sheets

(56) References Cited

U.S. PATENT DOCUMENTS

| | | | |
|---|---|---|---|
| 2007/0239092 A1* | 10/2007 | Ross | A61F 5/28 602/20 |
| 2008/0039752 A1* | 2/2008 | Rousso | A61H 7/001 601/134 |
| 2009/0177129 A1* | 7/2009 | Chan | A61H 23/0254 601/112 |
| 2009/0306561 A1* | 12/2009 | Naganuma | A61H 7/004 601/137 |
| 2013/0116606 A1* | 5/2013 | Cordo | A61H 23/0263 601/46 |
| 2016/0271009 A1* | 9/2016 | Giraud | A61H 23/006 |

* cited by examiner

TREMOR REDUCTION SYSTEM AND DEVICE

CROSS REFERENCE TO RELATED APPLICATION

This application claims the benefits of U.S. Provisional Application No. 61/887,675, filed Oct. 7, 2013.

FIELD OF THE INVENTION

The present invention relates generally to a body tremor reduction device and, more specifically, to a device arranged to apply pressure to a selective group of muscles and tendons on a human body.

BACKGROUND OF THE INVENTION

Traditionally surgery and medication are used to control tremor on a human body with varying success. Splints, braces, slings and bandaging are also employed to provide a measure of tremor reduction. However, these methods can be uncomfortable and cumbersome, and restrictive in performing functions such as eating, writing and dressing.

The present invention provides a different approach to tremor control.

SUMMARY OF THE INVENTION

The present invention provides a mechanical device arranged to contact a part of the human body for selectively applying pressure to muscle and tendon groups in order to reduce tremor.

One aspect of the present invention is a device for applying pressuring force to a part of a human body. The device comprises:

a mechanical flap arranged to apply a pressuring force on the part of the human body at a location; and a movable member configured to cause the mechanical flap to adjust the pressuring force.

According to an embodiment of the present invention, the device further comprises a case, wherein the mechanical flap is pivotably mounted on the case at a flap angle and wherein the case comprises a channel and the movable member comprises a movable rod locatable in the channel at a plurality of positions for changing the flap angle so as to adjust the pressuring force.

According to an embodiment of the present invention, the device further comprises a contacting member operatively connected to the mechanical flap, wherein the rod comprises a tapered section and the contacting member is arranged to contact the tapered section of the movable rod for changing the flap angle at least partly based on the positions.

According to an embodiment of the present invention, the case comprises a slot and a control rod operatively connected to the movable rod, and the control rod is configured to move to different locations in the slot for locating the movable rod to different positions in the channel.

According to an embodiment of the present invention, the contacting member comprises a rounded-head pin arranged to contact the tapered section.

According to an embodiment of the present invention, the mechanical flap comprises a flap portion and the case further comprises two mounting slots for connecting the case to a band configured to wrap around an arm so as to allow the flap portion to contact the part of the human body.

According to an embodiment of the present invention, the movable member is arranged to move along a direction to cause the mechanical flap to adjust the pressuring force, and the device further comprises:

a sensor arranged to sense a tremor adjacent to the location and to provide a sensed signal indicative of the tremor; and a driving mechanism, responsive to the sensed signal, configured to move the movable member along the direction for varying the pressuring force.

According to an embodiment of the present invention, the driving mechanism is configured to move the movable member bi-directionally along the direction via a linear drive.

According to an embodiment of the present invention, the device further comprises a timer configured to control the time duration and/or the pressuring force applied to the part of the human body.

According to an embodiment of the present invention, the timer is configured to reduce the pressuring force over a predetermined period of the time.

Another aspect of the present invention is a method of applying pressure to a part of a human body. The method comprises:

arranging a mechanical flap to contact and apply a pressuring force to the part of the human body, and operatively connecting a movable member to the mechanical flap for adjusting the pressuring force.

According to an embodiment of the present invention, the mechanical flap is pivotable mounted on a case at a flap angle, and the case comprises a channel and the movable member comprises a movable rod locatable in the channel at a plurality of positions for changing the flap angle to adjust the pressuring force, and the rod comprises a tapered section, the method further comprises connecting a contacting member to the mechanical flap, the contacting member arranged to contact the tapered section of the movable rod for changing the flap angle at least partly based on the positions.

According to an embodiment of the invention, the case comprises a slot and a control rod operatively connected to the movable rod, and wherein the control rod is configured to move to different locations in the slot for locating the movable rod to different positions in the channel, and the contacting member comprises a rounded-head pin arranged to contact the tapered section.

According to an embodiment of the present invention, the mechanical flap further comprises a flap portion and wherein the case further comprises two mounting slots for connecting the case to a band configured to wrap around an arm so as to allow the flap portion to contact the part of the human body.

According to an embodiment of the present invention, the movable member is arranged to move along a direction to cause the mechanical flap to adjust the pressuring force, and the method further comprises:

arranging a sensor adjacent to the location for sensing a tremor and for providing a sensed signal indicative of the tremor; and providing a driving mechanism, responsive to the sensed signal, configured to move the movable member along the direction for varying the pressuring force, wherein the driving mechanism is configured to move the movable member bi-directionally along the direction via a linear drive.

According to an embodiment of the present invention, the method further comprises providing a timer to the driving mechanism, the timer configured to control the time duration and/or the pressuring force applied to the part of the human body, wherein the timer is configured to reduce the pressuring force over a predetermined period of the time.

DETAILED DESCRIPTION OF THE INVENTION

The lower arm muscles contract and relax, together with the mass of the hand, forming a vibrating system with low damping. In effect, the hand mass and the arm muscles are analogous to a simple spring mass vibrating system, in which body chemicals supply muscle energy and the nerves activate muscles. If the spring is shortened while maintaining the same amount of vibratory energy, the amplitude of oscillation is reduced with a higher resonant frequency. The spring mass resonant frequency with low damping is roughly proportional to the square root of the spring tension per unit length. Therefore, by compressing a selective group of muscles at a location that is about one quarter of full muscle length, tremor vibration rate is roughly doubled and vibration amplitude is decreased substantially. Chemical energy provided to the shortened portion of the muscle is less than that of the entire muscle which further aids in reducing the tremor. Detrimental nerve-to-muscle response that reinforces the vibration may also be reduced at a higher resonant frequency.

The present invention provides a mechanical device configured to compress a selective group of muscles at a location of an arm in order to reduce the tremor vibration amplitude by shortening the segment of the muscles that contract and relax. The mechanical device can be made contact to the location of the inner arm by a band or another retaining mechanism.

Figure 1:
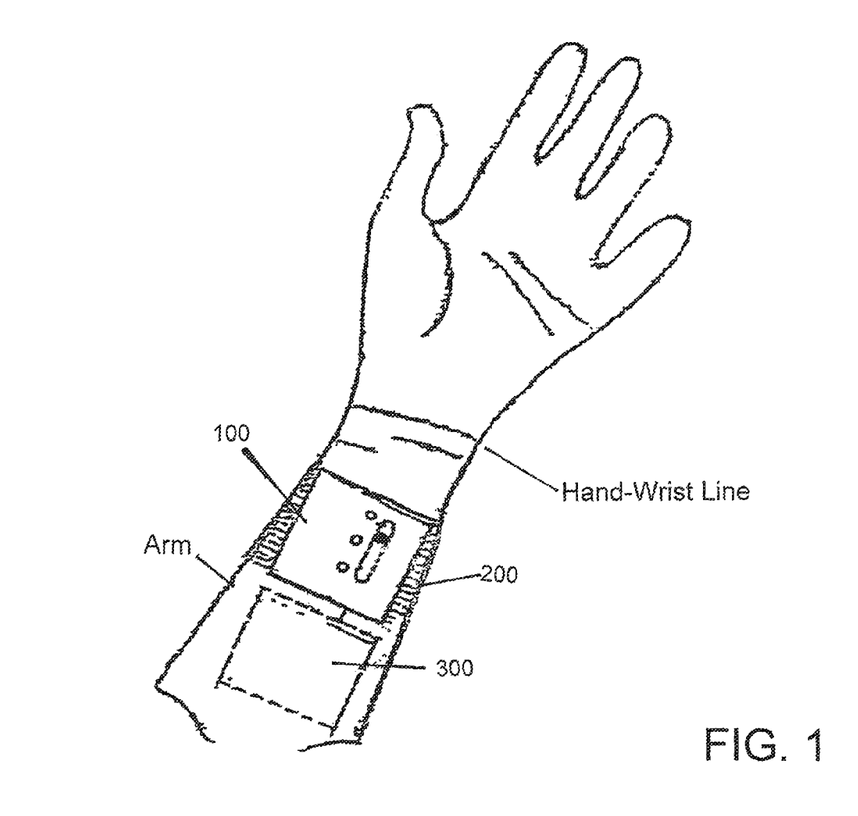
FIG. 1 shows a tremor reduction device according to an embodiment of the present invention.
Figure 2:
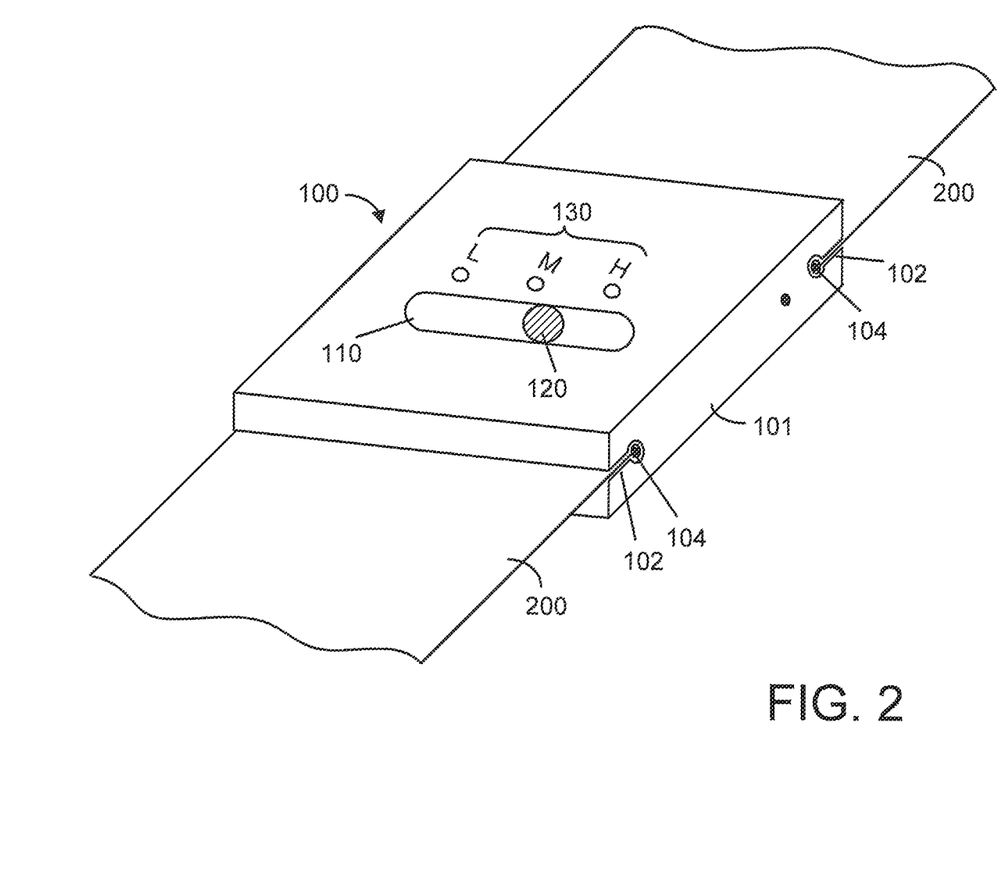
FIG. 2 is an isometric view of the tremor reduction device attached to a band.

FIG. 1 shows a tremor reduction device, according to an embodiment of the present invention, held onto the arm by a band. FIG. 2 shows an isometric view of the tremor reduction device. As shown in FIGS. 1 and 2, tremor reduction device 100 has a case 101, which is attached to a band 200. Tremor reduction device 100 is positioned at a location of the inner arm for selectively applying pressure to the muscles and tendons on the arm. For example, tremor reduction device 100 can be positioned about 2-5 inches from the hand-wrist line. Optionally, a controlling device 300 is operatively connected to tremor reduction device 100 for providing automatic tremor control, for example.

As shown in FIG. 2, tremor reduction device 100 has a sliding slot 110, in which a control rod 120 can be manually moved to different positions to change the pressure applied to the inner arm. For example, the pressure can be set to be low (L), medium (M) or high (H) as indicated by indicators 130. Control rod 120 is used to raise or release a flap that contacts with the arm at a pressure applying point (see FIG. 5). The control rod positions can be reset and released manually. The case 101 of tremor reduction device 100 has two slots 102 to be engaged with band 200 by bars 104. The shape of tremor reduction device 100 can be elliptical with rounded edges for greater comfort, for example. The back side of tremor control device 100 can also be contoured both for comfort and to counter the flap force against the case 101 of tremor reduction device 100. Case 101 can have an area approximately 2×2 inches and a depth about 6 inch.

Band 200 can be made of elastic, plastic, leather or other flexible materials. The two ends of the band that wraps around the arm can be joined by one or more fabric hook-and-loop fasteners, buckles, snaps or other securing means.

Figure 3:
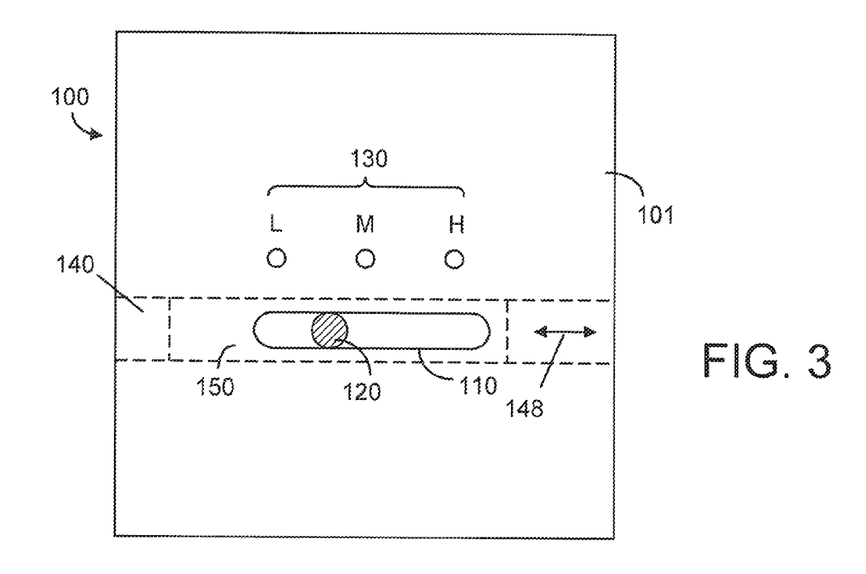
FIG. 3 is a front view of the tremor reduction device.
Figure 6:
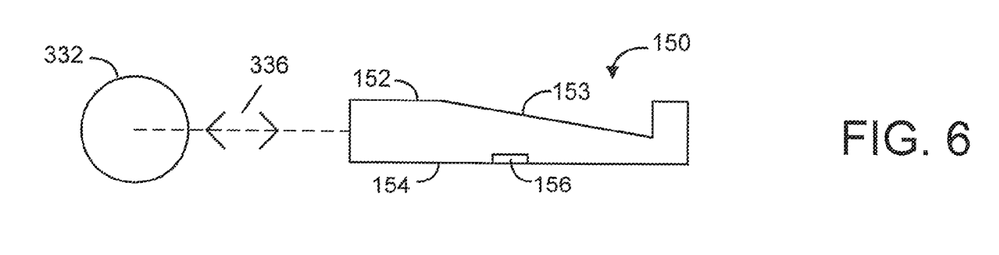
FIG. 6 shows a movable rod having a tapered section.

FIG. 3 shows a front view of the tremor reduction device. As shown in FIG. 3, tremor reduction device 100 has an inner channel 140 to allow movable rod 150 to move laterally and bi-directionally as indicated by arrow 148. Movable rod 150 can be moved by control rod 120 along sliding slot 110. As can be seen in FIG. 6, movable rod 150 can also be moved bi-directionally by a motor 332 (or other movement device) via a linear drive mechanism 336.

Figure 4:
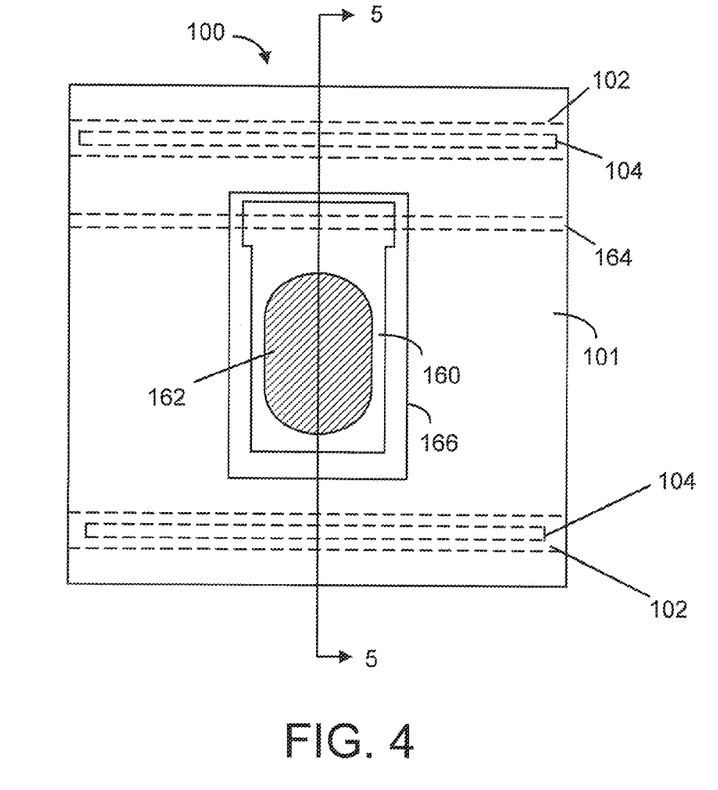
FIG. 4 is a back view of the tremor reduction device.
Figure 5:
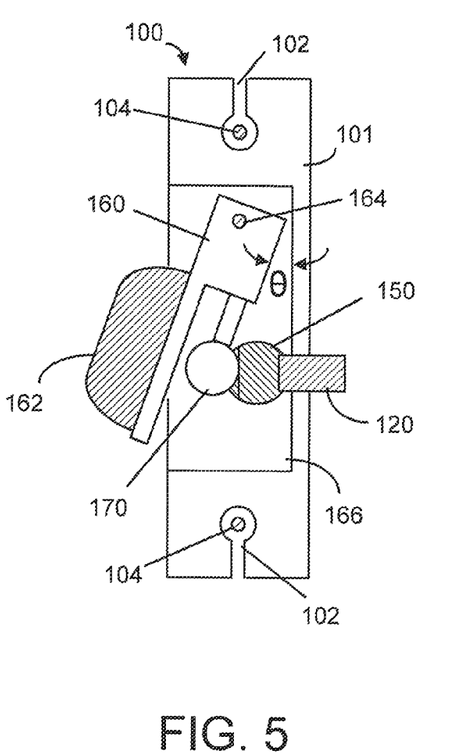
FIG. 5 is a cross sectional view of the tremor reduction device.

FIG. 4 shows a back view of the tremor reduction device. FIG. 5 is a cross sectional view of the tremor reduction device. As shown in FIGS. 4 and 5, tremor reduction device 100 has a flap opening 166 to accommodate a flap 160 and to allow one end of flap 160 to move in and out of the opening. Flap 160 has a flap portion 162 that contacts with the inner arm for applying pressure to the muscles and tendons around the contacting point. As shown in FIG. 5, flap 160 is pivotally mounted at a pivot rod 164. Flap 160 has a rounded head pin 170 arranged to be in contact with movable rod 150. As shown in FIG. 6, movable rod 150 has a tapered section 153 on side 152. On side 154, movable rod 150 has a dent 156 to be engaged with control rod 120 (see FIGS. 3 and 5). Depending on the positions of rounded head pin 170 in the tapered section 153, flap portion 162 can be closer to or further from surface 152 of movable rod 150. As control rod 120 is moved to different positions in sliding slot 110 (see FIG. 3), the flap angle θ can be increased or decreased. As the flap angle is increased from a small angle, such as 0 degree, to a larger angle, flap portion 162 compresses selective muscles and tendons and applies pressure to the flesh toward the arm and, more significantly, against the radial bone. The flap can be made of metal, plastic or other sturdy materials while the flap portion that contacts with the arm can be made of rubber or other compressible materials. FIGS. 4 and 5 also show the mounting slots 102 and bars 104 for attaching case 101 to a band (FIG. 2).

The flap pressure required to compress muscles and tendons against the radial bone is less than it is required to compress the flesh alone. The advantages of the reduced flap pressure are greater comfort and the minimal disturbance to the blood vessels and nerves around the pressure applying point. In addition, by choosing the flap positions, the compression on the muscles and tendons that control finger movement in normal activities can be avoided or minimized.

The dimensions of the flap can range from ¾ to 4 inches parallel to the arm and ½ to ⅝ inches across the arm, for example. A larger flap area may reduce pressure and could be more effective in clamping muscles and tendons.

Flaps with varying flexibility and different outlined contours can be interchanged in order to accommodate different users. For example, a smaller arm or wrist may require a smaller flap portion. Flap changing can be done by removing the pivot rod 164 (see FIGS. 4 and 5).

In an embodiment of the present invention, the tremor reduction device as illustrated in FIG. 1 to FIG. 6 can be used as a stand alone device to reduce tremors in limb and extremity.

In another embodiment of the present invention, the tremor reduction device can be used in conjunction with an automatic tremor detector and controller, such as controlling device 300 as depicted in FIG. 1. Controlling device 300 may have various functions as shown in FIG. 7.

Figure 7:
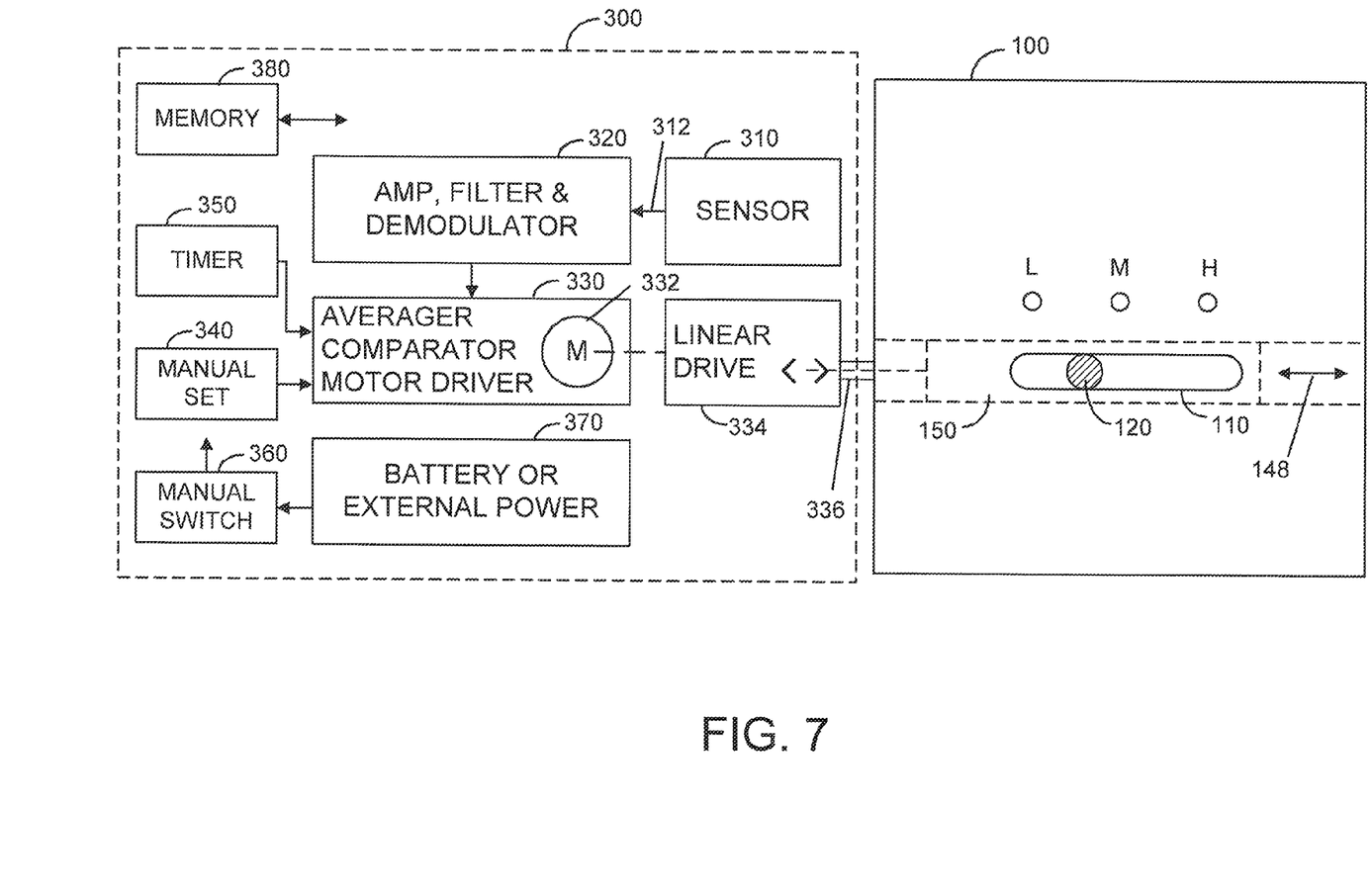
FIG. 7 is a functional diagram of the tremor reduction system, according to an embodiment of the present invention.

As shown in FIG. 7, controlling device 300 may comprise a vibration sensor 310, a signal processor 320, a driving circuit 330 with a motor 332, a linear drive 334, a linear drive mechanism 336, a battery or external power source 370, a switch 360, a manual set 340 and a timer 350. For example, vibration sensor 310 can be used to sense the tremors of the arm and provides a sense signal 312 to signal processor 320. Signal processor 320 may comprise an amplifier, a signal filtering circuit and a demodulator, for example, for processing the sense signal and providing a drive signal to driving circuit 330. Driving circuit 330 may comprise a signal averager, a comparator and a motor driver, for example. The motor driver is arranged to cause motor 332 to turn. Through linear drive 334, the rotational motion of motor 332 is translated into a linear motion in order to move movable rod 150 bi-directionally via linear drive mechanism 336. As rounded head pin 170 interacts with tapered section 153 on movable rod 150 driven by motor 332, one end of flap 160 is moved in and out of flap opening 166 and flap angle θ is changed accordingly (see FIG. 5). As such, controlling device 300 may be used to adjust the pressing force applied by flap portion 162 based on the tremor sensing by vibration sensor 310.

Vibration sensor 310 can be a coil disposed in relationship to a magnet, for example. As arm tremors vibrate the magnet relative to the coil, induced current in the coil can be used as a sense signal. Linear drive 334, which can be overridden by manual control, may have a thread screw to translate the rotational motion to the linear motion. Through linear drive mechanism 334, linear drive 334 moves movable rod 150 as a function of the comparator output, based on signals from manual set 340 and the signal averager in driving circuit 330, for example. An additional very long-term average signal may augment the manual setting. Furthermore, a timer 350 may be used to control the time duration and/or the force of the pressure. For example, timer 350 can be programmed to reduce the pressure gradually over a period of time, but the user may reset to increase the pressure or disable the timer if so desired. Timer 350, which can be mechanical or electronic, can be activated by the sense signal, for example.

The manual switch 360 can be used by a user to turn the controlling device 300 on or off.

As can be seen in FIGS. 5 and 6, flap portion 162, along with one end of flap 160, is pushed outward from flap opening 166 by control rod 120 via rounded head pin 170, which is made contact tapered section 153 of movable rod 150. When the tremor reduction device is in use, flap 160 is pushed back by the flesh on the arm.

Nevertheless, flap 160 is returned to flap opening 166 by a leaf spring, according to an embodiment of the present invention, It should be understood that control rod 120 in sliding slot 110 provides limit stops for movable rod 150. When a limit stop is reached, the current that drives motor 332 would rise sharply. This increase in the motor current can be used for rod control, eliminating the use of limit switches and the wiring between controlling device 300 and tremor reduction device 100, for example. In general, motor 332 is only used for positioning flap 160. Thus, a sleeper circuit (not shown) can be used to prolong the life of battery 370. In one embodiment of the present invention, a memory device 380 is used to store data relating to tremors and pressures for analysis purposes, for example.

In summary, the present invention provides a tremor reduction device having a flap arranged to contact a part of the human body, such as an arm for applying pressure to the muscles and/or tendons around the part of the human body. The tremor reduction device has a movable rod with a tapered section for varying the pressure applied by the flap to the part of the human body. The movable rod can be moved along a channel in the tremor reduction device by a manual control rod to various locations in a sliding slot for adjusting the pressure. In an embodiment of the present invention, the tremor reduction device is used in conjunction with a controlling device having a movement mechanism arranged to move the movable rod for pressure adjustment. The controlling device has a vibration sensor to sense tremors and to send a sense signal to a signal processor. The signal processor provides a driving signal to a driving circuit to turn on a motor. Through a linear drive, the motor moves the movable rode bi-directionally.

Thus, although the present invention has been described with respect to one or more embodiments thereof, it will be understood by those skilled in the art that the foregoing and various other changes, omissions and deviations in the form and detail thereof may be made without departing from the scope of this invention.

What is claimed is:

1. A device for applying pressure to a part of a human body, comprising:
   a case having a first case side and an opposing second case side;
   a mechanical flap pivotably mounted on the case, the mechanical flap comprising a flap portion at least partly located outside the case on the second case side arranged to contact with said part of the human body so as to apply a pressuring force on said part of the human body at a location in said part of the human body;
   a movable member at least partly located adjacent to a surface of the case on the first case side, the movable member mechanically linked to the mechanical flap, configured to cause the flap portion to adjust the pressuring force;
   wherein the mechanical flap is pivotably mounted on the case at a flap angle and wherein the case comprises a channel and the movable member comprises a movable rod locatable in the channel at a plurality of positions for changing the flap angle so as to adjust the pressuring force;
   further comprising a contacting member operatively connected to the mechanical flap, wherein the movable rod comprises a tapered section and the contacting member is arranged to contact the tapered section of the movable rod for changing the flap angle at least partly based on the positions; and
   wherein the case further comprises a slot adjacent to the surface of the case on the first case side and a control rod operatively connected to the movable rod, and wherein the control rod is configured to move to different locations in the slot for locating the movable rod to different positions in the channel.

2. The device according to claim 1, wherein the contacting member comprises a rounded-head pin arranged to contact the tapered section.

3. The device according to claim 1, wherein said part of the human body comprises an inner arm, and wherein the case further comprises two mounting slots for connecting the case to a band configured to wrap around an arm at an arm portion including the inner arm so as to allow the flap portion to contact said part of the human body.

4. The device according to claim 1, wherein the movable member is arranged to move along a direction to cause the mechanical flap to adjust the pressuring force, the device further comprising:
- a sensor arranged to sense a tremor adjacent to the location and to provide a sensed signal indicative of the tremor; and
- a driving mechanism, responsive to the sensed signal, configured to move the movable member along the direction for varying the pressuring force.

5. The device according to claim 4, wherein the driving mechanism is configured to move the movable member bi-directionally along the direction via a linear drive.

6. The device according to claim 4, further comprising a timer configured to control a time duration and/or the pressuring force applied to the part of the human body.

7. The device according to claim 6, wherein the timer is configured to reduce the pressuring force over a predetermined time period.

8. A method of applying pressuring force to a part of a human body, comprising:
- arranging a case having a first case side and an opposing second case side;
- pivotably mounting a mechanical flap to the case, the mechanical flap comprising a flap portion at least partly located outside the case on the second case side arranged to contact with said part of the human body so as to apply a pressuring force to said part of the human body at a location in said part of the human body,
- operatively connecting a movable member to the mechanical flap for adjusting the pressuring force, the movable member at least partly located partly adjacent to a surface of the case on the first case side;
- wherein the mechanical flap is pivotably mounted on a case at a flap angle, and wherein the case comprises a channel and the movable member comprises a movable rod locatable in the channel at a plurality of positions for changing the flap angle to adjust the pressuring force;
- wherein the movable rod comprises a tapered section, said method further comprising connecting a contacting member to the mechanical flap, the contacting member arranged to contact the tapered section of the movable rod for changing the flap angle at least partly based on the positions; and
- wherein the case further comprises a slot adjacent to the surface of the case on the first case side and a control rod operatively connected to the movable rod, and wherein the control rod is configured to move to different locations in the slot for locating the movable rod to different positions in the channel.

9. The method according to claim 8, wherein the contacting member comprises a rounded-head pin arranged to contact the tapered section.

10. The method according to claim 8, wherein said part of the human body comprises an inner arm, and wherein the case further comprises two mounting slots for connecting the case to a band configured to wrap around an arm at an arm portion including the inner arm so as to allow the flap portion to contact said part of the human body.

11. The method according to claim 8, wherein the movable member is arranged to move along a direction to cause the mechanical flap to adjust the pressuring force, said method further comprising:
- arranging a sensor adjacent to the location for sensing a tremor and for providing a sensed signal indicative of the tremor; and
- providing a driving mechanism, responsive to the sensed signal, configured to move the movable member along the direction for varying the pressuring force.

12. The method according to claim 11, wherein the driving mechanism is configured to move the movable member bi-directionally along the direction via a linear drive.

13. The method according to claim 11, further comprising providing a timer to the driving mechanism, a time configured to control the time duration and/or the pressuring force applied to the part of the human body.

14. The method according to claim 13, wherein the timer is configured to reduce the pressuring force over a predetermined time period.

* * * * *